(12) United States Patent
Abril et al.

(10) Patent No.: US 8,529,979 B2
(45) Date of Patent: Sep. 10, 2013

(54) STABLE EMULSIONS OF OILS IN AQUEOUS SOLUTIONS AND METHODS FOR PRODUCING SAME

(75) Inventors: Jesus Ruben Abril, Westminster, CO (US); George E. Stagnitti, Longmont, CO (US)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/791,714

(22) Filed: Jun. 1, 2010

(65) Prior Publication Data

US 2010/0298435 A1 Nov. 25, 2010

Related U.S. Application Data

(63) Continuation of application No. 10/518,957, filed as application No. PCT/US03/19108 on Jun. 18, 2003, now abandoned.

(60) Provisional application No. 60/389,813, filed on Jun. 18, 2002.

(51) Int. Cl.
*A23D 7/00* (2006.01)

(52) U.S. Cl.
USPC .......................................... 426/602; 426/601

(58) Field of Classification Search
USPC ................................................ 426/601–604
See application file for complete search history.

(56) References Cited

U.S. PATENT DOCUMENTS

| | | | |
|---|---|---|---|
| 4,637,937 A | 1/1987 | Terada et al. | |
| 5,080,921 A | 1/1992 | Reimer | |
| 5,130,242 A | 7/1992 | Barclay | |
| 5,156,875 A | 10/1992 | Monte | |
| 5,258,194 A | 11/1993 | Anderson et al. | |
| 5,302,408 A | 4/1994 | Cain et al. | |
| 5,324,445 A | 6/1994 | Langley et al. | |
| 5,340,594 A | 8/1994 | Barclay | |
| 5,550,156 A | 8/1996 | Kyle | |
| 5,658,767 A | 8/1997 | Kyle | |
| 6,034,130 A | 3/2000 | Wang et al. | |
| 6,140,374 A | 10/2000 | May et al. | |
| 6,190,721 B1 | 2/2001 | Kimura et al. | |
| 6,231,915 B1 | 5/2001 | van Amerongen et al. | |
| 6,348,610 B1 | 2/2002 | Martinez Force et al. | |
| 6,410,078 B1 | 6/2002 | Cain et al. | |
| 6,423,363 B1 | 7/2002 | Traska et al. | |
| 6,716,460 B2 | 4/2004 | Abril | |
| 6,737,084 B2 | 5/2004 | Crosby et al. | |
| 6,793,958 B2 | 9/2004 | Kuil et al. | |
| 7,029,717 B1 * | 4/2006 | Ojima et al. | 426/548 |
| 7,029,719 B1 | 4/2006 | Nakajima et al. | |
| 2002/0034557 A1 | 3/2002 | Crosby et al. | |
| 2002/0081366 A1 * | 6/2002 | Cain et al. | 426/601 |
| 2002/0182303 A1 | 12/2002 | Hotta et al. | |
| 2002/0197382 A1 | 12/2002 | Kuijpers et al. | |
| 2003/0039672 A1 | 2/2003 | Ginger et al. | |
| 2003/0198727 A1 | 10/2003 | Koike et al. | |
| 2005/0129739 A1 | 6/2005 | Kohn et al. | |

FOREIGN PATENT DOCUMENTS

| | | |
|---|---|---|
| DE | 196 44 518 A1 | 4/1998 |
| DE | 197 56 123 A1 | 6/1999 |
| DE | 100 13 156 A1 | 9/2001 |
| EP | 0 659 347 A1 | 6/1995 |
| JP | 46-4533 | 11/1971 |
| JP | 60-16573 A | 1/1985 |
| JP | 60-118164 A | 6/1985 |
| JP | 03-501206 W | 3/1991 |
| JP | 04-228051 A | 8/1992 |
| JP | 05-146270 A | 6/1993 |
| JP | 05-199837 A | 8/1993 |
| JP | 05-286845 A | 11/1993 |
| JP | 05-286846 A | 11/1993 |
| JP | 06-209704 A | 8/1994 |
| JP | 07-313055 A | 12/1995 |
| JP | 08-205772 A | 8/1996 |
| JP | 09-234015 A | 9/1997 |
| JP | 10-290929 A | 11/1998 |
| JP | 10-305222 A | 11/1998 |
| JP | 2001-192328 A | 7/2001 |
| JP | 2002-053671 A | 2/2002 |
| JP | 2002-510205 A | 4/2002 |
| JP | 2002-138297 A | 5/2002 |
| JP | 2002-517216 A | 6/2002 |
| JP | 2003-221332 A | 8/2003 |
| JP | 2005-503379 A | 2/2005 |
| WO | WO 89/02223 A1 | 3/1989 |
| WO | WO 98/55625 A1 | 12/1998 |
| WO | WO 99/29316 A1 | 6/1999 |
| WO | WO 99/63835 A1 | 12/1999 |
| WO | WO 99/65327 A1 | 12/1999 |
| WO | WO 01/08653 A1 | 2/2001 |
| WO | WO 01/49282 A2 | 7/2001 |
| WO | WO 01/80656 A1 | 11/2001 |
| WO | WO 03/013462 A1 | 2/2003 |

OTHER PUBLICATIONS

Extended European Search Report, which includes the European Search Result and European Search Opinion, for EP Application No. EP 11 17 1163, European Patent Office, Munich, Germany, mailed on Aug. 24, 2011, 6 pages.

(Continued)

*Primary Examiner* — Carolyn Paden

(74) *Attorney, Agent, or Firm* — Sterne, Kessler, Goldstein & Fox P.L.L.C.

(57) ABSTRACT

Methods for making highly stable, oxidation-resistant emulsions comprising an oil, an emulsifier, an emulsion stabilizer and water are provided. The invention is particularly well suited for oils that are susceptible to oxidation, such as long chain polyunsaturated fatty acid oils. The resulting emulsion is highly stable and resistant to oxidation, and is useful in a number of products and as a stand-alone product.

20 Claims, 1 Drawing Sheet

(56) References Cited

OTHER PUBLICATIONS

Office Action for European Application No. 03737159, dated Aug. 18, 2011, European Patent Office, Munich, Germany, 5 pages.
Firestone, D., editor. *Physical and Chemical Characteristics of Oils, Fats, and Waxes*, pp. 90, 91, 94, 95, AOCS Press, US (1999).
Gerlat, P., "Beverage Stabilizers," *Food Product Design: Applications*, 8 pages, Weeks Publishing Co., US (2000), available at http://www.foodproductdesign.com/articles/1000ap.html.
Gunstons, F. et al., *The Lipid Handbook*, Second Edition, pp. 88-89, Chapman & Hall, UK (1994).
Written Opinion for International Patent Application No. PCT/US03/19108, IPEA/US, Alexandria, VA, mailed Aug. 25, 2004.
International Search Report for International Application No. PCT/US03/19108, ISA/US, Alexandria, VA, mailed on Nov. 20, 2003.
International Preliminary Examination Report for International Application No. PCT/US03/19108, IPEA/US, Alexandria, VA, issued May 4, 2005.
Patent Abstracts of Japan, English language abstract for Japanese Patent Publication No. JP 2001-192328 A, published Jul. 17, 2001.
English language abstract for German Patent Publication No. DE 100 13 156 A1, published Sep. 20, 2001.
Patent Abstracts of Japan, English language abstract for Japanese Patent Publication No. JP 2002-138297 A, published May 14, 2002.
Patent Abstracts of Japan, English language abstract for Japanese Patent Publication No. JP 2002-053671 A, published Feb. 19, 2002.
Patent Abstracts of Japan, English language abstract for Japanese Patent Publication No. JP 2003-221332 A, published Aug. 5, 2003.
Dialog File 351, Accession No. 431056, Derwent WPI Engligh language abstract for JP 46-004533 A, published Nov. 16, 1971.
Patent Abstracts of Japan, English language abstract for Japanese Patent Publication No. JP 10-290929 A, published Nov. 4, 1998.
Patent Abstracts of Japan, English language abstract for Japanese Patent Publication No. JP 04-228051, published Aug. 18, 1992.
Patent Abstracts of Japan, English language abstract for Japanese Patent Publication No. JP 05-146270 A, published Jun. 15, 1993.
Patent Abstracts of Japan, English language abstract for Japanese Patent Publication No. JP 05-199837 A, published Aug. 10, 1993.
Patent Abstracts of Japan, English language abstract for Japanese Patent Publication No. JP 05-286845 A, published Nov. 2, 1993.
Patent Abstracts of Japan, English language abstract for Japanese Patent Publication No. JP 06-209704 A, published Aug. 2, 1994.
Patent Abstracts of Japan, English language abstract for Japanese Patent Publication No. JP 07-313055 A, published Dec. 5, 1995.
Patent Abstracts of Japan, English language abstract for Japanese Patent Publication No. JP 08-205772 A, published Aug. 13, 1996.
Patent Abstracts of Japan, English language abstract for JP 09-234015 A, published Sep. 9, 1997.
Patent Abstracts of Japan, English language abstract for Japanese Patent Publication No. JP 10-305222 A, published Nov. 17, 1998.
English language abstract for German Patent Publication No. DE 197 56 123 A1, published Jun. 24, 1999.
Patent Abstracts of Japan, English language abstract for Japanese Patent Publication No. JP 05-286846 A, published Nov. 2, 1993.
Patent Abstracts of Japan, English language abstract for Japanese Patent Publication No. JP 60-1181642 A, published Jun. 25, 1985.
Patent Abstracts of Japan, English language abstract for Japanese Patent Publication No. JP 60-16573 A, published Jan. 28, 1985.

* cited by examiner

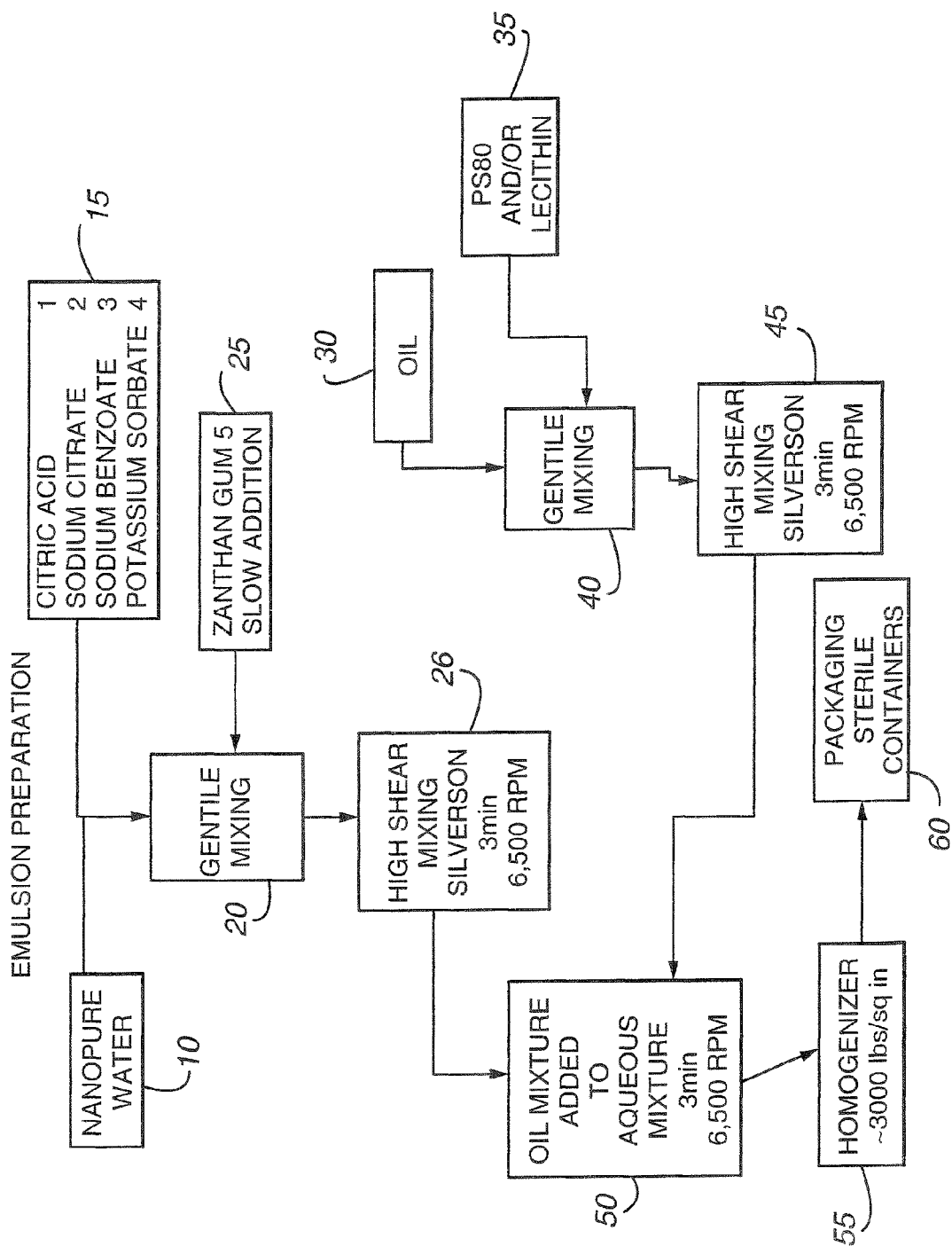

STABLE EMULSIONS OF OILS IN AQUEOUS SOLUTIONS AND METHODS FOR PRODUCING SAME

CROSS-REFERENCE TO RELATED APPLICATIONS

This application is a continuation of U.S. patent application Ser. No. 10/518,957, filed Jun. 27, 2005, now abandoned; which is a 371 of PCT/US03/19108, filed Jun. 18, 2003; which claims benefit of 60/389,813, filed Jun. 18, 2002

FIELD OF THE INVENTION

The present invention is directed to oil-in-water emulsions, and in particular, emulsions that help protect oils from oxidation, especially oils that are susceptible to oxidation.

BACKGROUND OF THE INVENTION

It is desirable to form oil-in-water emulsions, and various techniques have been proposed to accomplish this task.

In the past, oil and polysorbate (or lecithin) and water have been combined to produce an emulsion, but the results have been unsatisfactory. The oil phase separated out of the mixture after relatively short periods of time and off-odors and off-tastes that developed indicated that oxidation products of the oil had formed. Oil and xanthan gum and water mixtures are only temporarily stable, like those found in salad dressings. Emulsification of oil can also be achieved through the addition of water to the oil, combined with strong, lengthy agitation, but the resulting emulsion is very unstable.

Newer approaches have involved the use of proteins as emulsifiers. However, these emulsions are not stable over a wide range of pH conditions. For example, a protein that forms a stable emulsion under low pH conditions (e.g., pH 4) would denature at higher pH (e.g., pH 7), and would no longer act as an emulsifier. Another problem with protein emulsifiers is that upon heating, the protein is destabilized by its conformational change.

The above-described techniques have failed because of the difficulty in maintaining the emulsification and the stability of the oils. The emulsification of the aqueous and oil phases is usually temporary, and the oil/water mixture typically reverts to separate aqueous and oil phases without continued agitation. When the oil is susceptible to oxidation, as is the case with long chain polyunsaturated fatty acids (LCPUFA), stability of the product is also diminished due to the more rapid oxidation of the oils, and in particular, the LCPUFA oils. Protein-based emulsions are not stable over the wide range of pH and temperature conditions found in foods.

It would be advantageous to incorporate LCPUFA-containing oils in aqueous mixtures, such as aqueous food, cosmetic, pharmaceutical and industrial product matrices, without having the oil and water separate into two distinct phases. It would be advantageous to find ways to stabilize an oil-in-water emulsion over a long period of time, in other words, to form an emulsion that is physically stable (e.g., the oil and the water do not phase separate) for at least 30 days. It would be advantageous if the oil is protected by the emulsion from oxidation, in particular, when the oil is susceptible to oxidation, such as a LCPUFA oil.

SUMMARY OF THE INVENTION

The present invention is directed toward an oil emulsion. The emulsion includes an oil component, an emulsifier, an emulsion stabilizer, and water. The oil component can include polyunsaturated fatty acids, such as polyunsaturated fatty acids having at least three double bonds and a chain length of at least 18 carbons. Exemplary oil components include linolenic acid, stearidonic acid, arachidonic acid, eicosapentaenoic acid, docosapentaenoic acid, docosahexaenoic acid and mixtures thereof.

The oil component can be an oil from plants, genetically modified plants, microbial oils, genetically modified microbial oils, fish oils and mixtures thereof. Such plants can include algae, flaxseeds, rapeseeds, corn, evening primrose, soy, sunflower, safflower, palm, olive, canola, borage, and mixtures thereof. When such plants are genetically modified, the genetic modifications can include the introduction or modification of polyketide synthase genes. The oil component can also include an oil from a microbial source such as Thraustochytriales, dinoflagellates, and fungal sources.

In one embodiment, the emulsifier is selected from the group of polysorbate esters, lecithin, monoglycerides, diglycerides, organic acid esters of monoglycerides, propylene glycol esters of fatty acids, polyglycerol esters of fatty acids, propylene glycol monostearate, sorbitan monostearate, sorbitan trioleate, sodium lauryl sulfate and mixtures thereof. In one embodiment, the emulsifier and the oil can be from the same source.

In particular embodiments of the present invention, the stabilizer can be selected from the group of xanthan gum, alginate, gellan gum, carboxymethylcellulose, chitin and mixtures thereof.

The weight ratio of the oil component to the emulsifier can be between about 1:1 and about 99:1, and is preferably about 6:1. The ratio of water to emulsion stabilizer can be between about 1:0.1 and about 1:0.001. The ratio of oil component to water can be between about 2:1 and about 1:25.

Oil emulsions of the present invention are highly stable and can be physically and/or chemically stable for at least about 30 days.

The emulsion of the present invention can be an oil-in-water emulsion. Further, the emulsion can be produced without having been heat treated. The emulsion can also have a total bacteria count of less than 20 MPN/gram. In other embodiments, the oil emulsion can include an antimicrobial component, such as propylene glycol, potassium sorbate, sodium benzoate, ascorbic acid, phosphoric acid, citric acid and mixtures thereof.

The emulsion of the present invention can also include functionally active ingredients, such as flavors, pigments, sweeteners and anti-oxidants. The emulsion can also include bioactive ingredients, such as vitamins, minerals, pre-biotic compounds, pro-biotic compounds and nutraceuticals.

Other embodiments of the present invention include food products, cosmetic products, pharmaceutical products, nutriceutical products, and industrial products that include the oil emulsions of the invention.

Alternative embodiments of the present invention include a method for forming an emulsion. The method includes combining an oil component, an emulsifier, an emulsion stabilizer and water. In one embodiment, the oil component and emulsifier are combined; the emulsion stabilizer and the water are combined; and then, the oil component/emulsifier combination and the emulsion stabilizer/water combination are combined. The various components of the emulsion can be combined with high shear mixing.

In a preferred embodiment of the present invention, an oil emulsion is provided. The emulsion includes an oil component that includes polyunsaturated fatty acids having at least three double bonds and a chain length of at least 18 carbons.

The emulsion further includes an emulsifier, an emulsion stabilizer, water and an antimicrobial component. In this embodiment, the weight ratio of oil component to emulsifier is between about 1:1 and about 99:1. The ratio of water to emulsion stabilizer is between about 1:0.1 and about 1:0.001. The ratio of oil component to water is between about 2:1 and about 1:25. This oil emulsion composition is physically and chemically stable for at least about 30 days.

BRIEF DESCRIPTION OF THE DRAWINGS

FIG. 1 is a flowsheet of an example of preparation of an emulsion of the present invention.

DETAILED DESCRIPTION OF THE INVENTION

In accordance with one embodiment of the present invention, a method is provided for forming stable emulsions, particularly including LCPUFA. The method includes the step of mixing at least four ingredients: (1) oil; (2) emulsion stabilizer; (3) emulsifier; and (4) water. The resulting emulsion is an oil-in-water emulsion with water as the continuous phase. It is believed that the emulsion stabilizer assists in maintaining the long-term stability of the emulsion without the need to agitate the solution continually for even distribution, preventing the oxidation of the LCPUFA oils and maintaining the integrity of the oils, thereby enhancing a longer shelf life of the product. Preferably, the emulsion is stable for at least 30 days, and more preferably for at least 60 days. The resulting emulsions are very stable over a wide range of pH conditions and temperatures, and the LCPUFA oils are highly protected from oxidation. These emulsions can exist as standalone products and can easily be incorporated into a wide range of products, including food, personal care and industrial products (e.g., human foods, animal feeds, pharmaceuticals, nutraceuticals, cosmetics, industrial products, etc.). A particular advantage of the products of the present invention is that they can be uniformly dispersed in a wide variety of end products.

The oil component of emulsions of the present invention can include any oil, preferably, any vegetable or microbial oil, including for example, oils having LCPUFA. Long chain PUFA oils can include any oil containing a fatty acid with at least two, and more preferably three or more double bonds, and a chain length of at least 18 carbons. Examples of LCPUFA oils include oils containing the fatty acids linolenic acid (18:3n-3), stearidonic acid (18:4n-3) arachidonic acid (20:4n-6), eicosapentaenoic acid (20:5n-3), docosapentaenoic acid (22:5n-3 and 22:5n-6) and docosahexaenoic acid (22:6n-3). Examples of these oils include oils from fish oils, microbial oils (e.g. from Thraustochytriales, such as *Schizochytrium* and *Thraustochytrium*, from dinoflagellates such as *Crypthecodinium*, and from fungal sources such as *Mortierella*), plants, and oilseeds, as well as genetically modified fish oils, microbial oils, plants, and oilseeds.

Sources of fatty acids (e.g., omega-3 and omega-6 LCPUFA) can include oils from animal, plant and microbial sources. As used herein, the term "oil" is used broadly to include fats and oils in various forms. The oil must be capable of emulsification. Preferred oils include triacylglycerol and ethyl ester forms of LCPUFA. Typically, the oils will be a mixture of different substances, such as triacylglycerols, ethyl esters, free fatty acids, phospholipids, sterols, etc. Such mixtures can be purified, if desired. Examples of animal sources include aquatic animals (e.g., fish, marine mammals, crustaceans, rotifers, etc.) and oils extracted from animal tissues (e.g., brain, liver, eyes, etc.). Examples of plant and microbial sources include algae, flaxseeds, rapeseeds, corn, evening primrose, soy, sunflower, safflower, palm, olive, canola and borage. A preferred source is aquatic algae such as algae of the order Thraustochytriales, and preferably algae of the genus *Thraustochytrium* and *Schizochytrium*. It should be noted that many experts agree that *Ulkenia* is not a separate genus from *Thraustochytrium* and *Schizochytrium*. As used herein, the genera *Thraustochytrium* and *Schizochytrium* will include *Ulkenia*. Information regarding such algae can be found in U.S. Pat. Nos. 5,130,242 and 5,340,594, which are incorporated herein by reference in their entirety. Another preferred source is the dinoflagellate of the genus *Crypthecodinium*. Information regarding *Crypthecodinium* can be found in U.S. Pat. Nos. 5,407,957; 5,711,983; 5,397,591; and 5,492,938, which are incorporated herein by reference in their entirety. Information regarding *Mortierella* can be found in U.S. Pat. Nos. 5,658,767 and 5,583,019, which are incorporated herein by reference in their entirety.

Plant and microbial sources can include genetically modified plants and microorganisms, and preferably include genetic modified plants and microorganisms with increased or newly introduced production of PUFAs by the introduction or modification of a polyketide synthase system (PKS system). Information regarding genetic modifications involving PKS systems can be found in U.S. Pat. No. 6,566,583, entitled "Schizochytrium PKS Genes" issued May 20, 3003; PCT Application No, US00/00956 entitled "Schizochytrium PKS Genes" filed Jan. 14, 2000; U.S. patent application Ser. No. 10/124,807 entitled "Product and Process for Transformation of Thraustochytriales Microorganism" filed Apr. 16, 2002; PCT Patent Application No. PCT/US02/12040 entitled "Product and Process for Transformation of Thraustochytriales Microorganism" filed Apr. 16, 2002; U.S. patent application Ser. No. 10/124,800 entitled "PUFA Polyketide Synthase Systems and Uses Thereof" filed Apr. 16, 2002; and PCT Patent Application No. PCT/US02/12254 entitled "PUFA Polyketide Synthase Systems and Uses Thereof" filed Apr. 16, 2002; which are incorporated herein by reference in their entirety.

Oils containing the desired fatty acids can be extracted from the various sources by any suitable means, such as by supercritical fluid extraction or by extraction with solvents such as chloroform, hexane, methylene chloride, methanol and the like. Alternatively, the oils can be extracted using extraction techniques, such as are described in U.S. patent application Ser. No. 09/766,500 and PCT Patent Application Serial No. US01/01806 now U.S. Pat. No. 6,750,048, both entitled "Solventless Extraction Process" and both filed Jan. 19, 2001, both of which are incorporated herein by reference in their entirety. Lecithins can be extracted by any suitable technique, and are obtainable from many of the same sources from which the oils can be obtained. In a preferred embodiment of the present invention, lecithin, which is useful as an emulsifier, and oil are obtained from the same source. The lecithin and oil may be extracted together, or separately extracted and remixed to form the emulsion. Additional extraction and/or purification techniques are taught in PCT Patent Application Serial No. US01/12047 entitled "Method for the Fractionation of Oil and Polar Lipid-Containing Native Raw Materials" filed Apr. 12, 2001; PCT Patent Application Serial No. US01/12849 entitled "Method for the Fractionation of Oil and Polar Lipid-Containing Native Raw Materials Using Water-Soluble Organic Solvent and Centrifugation" filed Apr. 12, 2001; PCT/US02/15479 which claims priority from U.S. Provisional Patent Application Ser. No. 60/291,484 entitled "Production and Use of a Polar Lipid-Rich Fraction Containing Stearidonic Acid and Gamma Linolenic Acid from Plant Seeds and Microbes filed May 14, 2001; PCT/US02/15454 which claims priority from U.S. Provisional Patent Application Ser. No. 60/290,899 entitled "Production and Use of a Polar-Lipid Fraction Containing Omega-3 and/or Omega-6 Highly Unsaturated Fatty Acids from Microbes, Genetically Modified Plant Seeds and Marine Organisms" filed May 14, 2001; U.S. Pat. No. 6,399,803 entitled "Process for Separating a Triglyceride Comprising a Docosahexaenoic Acid Residue from a Mixture of Triglycerides" issued Jun. 4, 2002 filed Feb. 17, 2000; and PCT Patent Application Serial No. US01/01010 entitled "Process for Making an Enriched Mixture of Polyunsaturated Fatty Acid Esters" filed Jan. 1, 2001; all of which are incorporated herein by reference in their entirety. The extracted oils and lecithins can be evaporated under reduced pressure to produce a sample of concentrated oil material.

In emulsions of the present invention, the oil is typically present in an amount from about 5 wt. % to about 50 wt. %, more preferably from about 10 wt. % to about 40 wt. %, and even more preferably from about 20 wt. % to about 30 wt. %.

The emulsifier of emulsions of the present invention can include any emulsifier, including polysorbate esters, lecithin, monoglycerides, diglycerides, organic acid esters of monoglycerides, propylene glycol esters of fatty acids, polyglycerol esters of fatty acids, propylene glycol monostearate, sorbitan monostearate, sorbitan trioleate, and sodium lauryl sulfate. In a preferred embodiment of the present invention, a polysorbate ester (e.g., polyethylene sorbitan monooleate (Polysorbate 80), polyoxyethylene sorbitan monolaurate (Polysorbate 20), polyoxyethylene sorbitan tristearate (Polysorbate 65) or Polysorbate 60) is used as the emulsifier. In another preferred embodiment, the emulsifier can be a lecithin. Lecithins can be extracted from plant seeds, (e.g., soy lecithins), and can be extracted from eggs, milk, microbes or animal sources.

In emulsions of the present invention, the emulsifier is typically present in an amount from about 1 wt. % to about 20 wt. %, more preferably from about 8 wt. % to about 15 wt. %, and even more preferably from about 2 wt. % to about 6 wt. %.

The emulsion stabilizer of the present invention functions to further stabilize the emulsion compared to the emulsion in the absence of the stabilizer. The stabilizer can also function as a thickener of the emulsion. The emulsion stabilizer can be selected from xanthan gum, alginate, gellan gum, carboxymethylcellulose and chitin. In a preferred embodiment of the present invention, xanthan gum is used as the stabilizer.

In emulsions of the present invention, the emulsion stabilizer is typically present in an amount from about 0.1 wt. % to about 2 wt. %, more preferably from about 0.2 wt. % to about 0.8 wt. %, and even more preferably from about 0.3 wt. % to about 0.5 wt. %.

Emulsions of the present invention also include water. Water is typically present in an amount from about 10 wt. % to about 90 wt. %, more preferably from about 20 wt. % to about 80 wt. %, and even more preferably from about 50 wt. % to about 70 wt. %.

Emulsions of the present invention are highly stable in terms of both physical stability (i.e., lack of separation of components) and chemical stability (i.e., lack of oxidation of the oil component). Physical stability can be measured in a variety of ways. Simple visual observation of physical separation or "creaming" is an indication of separation. In preferred embodiments of the invention, no observable phase separation occurs after storage at 4 C, and more preferably after storage at room temperature (i.e., about 22 C), within 30 days, more preferably within 90 days, and more preferably within 180 days.

Another measure of physical stability is a lack of change in the particle size of micelles formed in the emulsion. As emulsions separate, the size of micelles becomes greater. In preferred embodiments of the invention, the particle size of micelles will not increase more than about 15%, more preferably not more than about 25%, more preferably not more than about 30%, more preferably not more than about 40%, and more preferably not more than about 50%, after storage at 4 C within 30 days, more preferably within 90 days, and more preferably within 180 days.

Chemical stability of an emulsion can be measured in terms of oxidation of any of the species of the oil component, including linolenic acid, stearidonic acid, arachidonic acid, eicosapentaenoic acid, docosapentaenoic acid and docosahexaenoic acid. Oxidation can be measured by the production of secondary products of oxidation, such as by measuring peroxide values, anisidine values, or alkenal values or by conducting a headspace analysis. In preferred embodiments, for any one or more of these various measures of oxidation, the value of the measure after storage at room temperature (i.e., about 22 C) for 30 days will increase less than about 20% by 60 days and/or less than about 50% by 90 days.

Another aspect of the physical and chemical stability of the invention is that the emulsions of the present invention can meet one or more of the physical or chemical stability parameters identified above over a wide range of pH conditions. More specifically, such parameters can be met over a pH range of about 3 to about 8, more preferably from about 3 to about 7, more preferably from about 3 to about 4.

Another aspect of the physical and chemical stability of the invention is that the emulsions of the present invention can meet one or more of the physical or chemical stability parameters identified above over a wide range of temperature conditions. More specifically, such parameters can be met over a temperature range of up to about room temperature (i.e., about 22 C), emulsions will be most stable at refrigeration temperature of about 4 C.

Emulsions of the present invention can be prepared by mixing the emulsifier with the oil in an initial step. Preferably, the weight ratio of oil to emulsifier is between about 1:1 and about 99:1, more preferably in a range from about 3:1 to about 50:1, more preferably in a range from about 4:1 to about 25:1, more preferably in a range from about 5:1 to about 10:1, more preferably in a ratio of about 6:1. Mixing can be facilitated by heating the mixture, for example, to about 6° C. for about 5 minutes, but can also be mixed at room temperature.

In an independent step of the process of preparing the emulsion, water and an emulsion stabilizer are mixed. Before this step, however, additional components that are water soluble, such as antimicrobial compounds like citric acid, sodium benzoate, and potassium sorbate, can be added to the water. A preferred weight ratio of water to emulsion stabilizer is in the range of about 1:0.1 to about 1:0.001, with a more preferred range of about 1:0.05 to about 1:0.005.

The oil/emulsifier mixture and the water/emulsion stabilizer are then combined. Preferably, these two mixtures are combined to achieve an oil to water ratio of between about 2:1 to about 1:25. Typically, this combination can be made at room temperature for ease of preparation and to avoid unnecessary temperature stress on the oil. However, mild heating (e.g., 35 C to 40 C) can be used to facilitate combining the mixtures. Mixing of the oil-based and water-based components can be done with a high shear mixer to form an emulsion. At that point, the emulsion can be homogenized in a homogenizer, preferably at 3000-4000 psi. The resulting product can then be packaged or used in other applications as discussed below.

A further aspect of the present invention is that emulsions of the invention have low microbial content even without being heat treated (i.e., pasteurized). For example, pasteurization is typically conducted at high temperatures (about 180 F) for about 15 seconds. Other known heat treatments include VAT, HTST, UHT and retorting. Non-pasteurized compositions of the present invention have low microbial contents. For example, emulsions of the present invention can have no detectable *Pseudomonas* or *Salmonella*. In addition, the emulsions can have a total bacteria count of <20 Most Probable Number ("MPN")/gram; a total *Coliform* and *E. coli* count of <20 MPN/gram; a yeast and mold count of <20 MPN/gram; and/or a *Staphylococcus aureus* count of <10 Colony Forming Units ("CFU")/gram. Low microbial content can be achieved by the inclusion of antimicrobial agents, such as propylene glycol, potassium sorbate, sodium benzoate, ascorbic acid, phosphoric acid or citric acid in the composition. Snot antimicrobial agents can be included in the composition in amounts up to the maximum allowable amount in food compositions. For example, compositions of the invention can include an antimicrobial agent in an amount of between about 0.05 and about 0.1% w/w.

In a preferred embodiment of the present invention, additional functionally active ingredients (e.g. flavors, pigments, sweeteners or antioxidants) or bioactive ingredients (e.g. vitamins, minerals, pre-biotic compounds, pro-biotic compounds or other nutraceutical compounds) can be incorporated in the emulsion. All such ingredients will be used following the recommendations of the manufacturer/supplier, as well as applicable governmental regulatory restrictions. These ingredients can be in either solid-powder or liquid form. Such additional functionally active ingredients can be incorporated in the emulsion or if the emulsion will be used in a food matrix, the additional ingredients can be added to the food matrix before addition of the emulsion to the food matrix. When the additional functionally active ingredients are added first to the emulsion, they can be added to either the oil phase or the water phase (depending on whether they are more oil or water soluble), but are preferably added to the oil phase. The ingredients can be added with moderate agitation until fully dispersed in the phase being used. Some such additional ingredients, such as flavors and pigments, will complement flavors and colors in foods to which emulsions containing them are added. In addition, such additives can mask marine flavors contributed by the oils or emulsification agents.

Flavors and pigments of all types can be included in emulsions of the invention with the exception of pigments containing iron as part of the molecule and flavors and pigments having low levels of metal contaminants, such as iron and copper.

In a preferred embodiment of the present invention, an LCPUFA emulsion is incorporated into liquid food products such as beverages (e.g., fruit juices and multivitamin syrups), into high moisture foods such as dairy products (e.g. yogurts), liquid pancake mixes and baby foods, into intermediate moisture foods such as health food bars and cheese, into processed meats (e.g. sausages), and as an ingredient in the preparation of baked goods (e.g., bread) or cereals. The emulsion can also be used both functionally and as a source of LCPUFA in cosmetic and personal care applications and in industrial applications. An advantage of the emulsion of the present invention is that it can be uniformly dispersed in a wide variety of end products.

With reference to FIG. 1, an example of preparation of an emulsion of the present invention is described. Nanopure water 10 is mixed with citric acid, sodium citrate, sodium benzoate, and potassium sorbate 15 by gentle mixing 20. Xanthan gum 25 is slowly added during the mixing process 20. The resulting aqueous mixture is subjected to high shear mixing 26 in a Silverson mixer at 6,500 rpm for 3 minutes Separately, the oil component 30 and the emulsifier 35, either polysorbate 80 and/or lecithin are gently mixed 40. The mixture of oil and emulsifier is then subjected to high shear mixing 45 in a Silverson mixer at 6,500 rpm for 3 minutes. The oil-based mixture from the high shear mixing 45 is added to the aqueous mixture from the high shear mixing 26. The oil mixture and aqueous mixture are subjected to high shear mixing 50 at 6,500 rpm for 3 minutes. The resulting composition is processed in a homogenizer 55 at about 3,000 psi. The composition is then packaged in sterile containers 60.

This application hereby incorporates by reference U.S. Provisional Application Ser. No. 60/389,813, filed Tune 18, 2002.

The following experimental results are provided for the purposes of illustration and are not intended to limit the scope of the invention.

EXAMPLES

Example 1

This example illustrates the preparation of an emulsion of the present invention, and its stability over time and when used in a food application.

A total of 75 grams of DHA-rich oil (DHA GOLD™ oil) extracted from the marine microorganism *Schizochytrium* sp. was added to 25 grams of polysorbate 80. The solution was heated to 60° C. for five minutes and mixed to dissolve the polysorbate. In a separate flask, 150 mg xanthan gum was mixed with 25 grams of water and vortexed. A new solution was made by taking 5 grams of the DHA GOLD oil/polysorbate solution and mixing with the entire 25+ grams of the water/xanthan gum solution. The new mixture was mixed and then heated at 60° C. for 1 minute to form the emulsion. The resulting mixture was stored in a refrigerator (4° C.) for 30 days. At the end of 30 days, no phase separation of the oil was observed. Odor evaluation of the emulsion indicated no formation of fishy odors—the emulsion was essentially odorless.

To test the effects of the emulsified mixture, 16.8 grams of the emulsion formed above was added to 437 grams of liquid egg substitute product and mixed. The egg product was then cooked to produce scrambled eggs. The resulting mixture provided 99.12 mg/DHA per serving (serving size=56 g liquid). No difference could be detected in taste or odor between the cooked egg substitute containing the DHA-oil emulsion and cooked egg substitute without any DHA-oil emulsion.

Example 2

This example illustrates the composition of a lecithin based emulsion of the present invention in Table 1.

TABLE 1

| Lecithin Based Emulsion | |
|---|---|
| Component | Wt. Percent |
| DHASCO-S ®*: DHA-containing oil | 27.91 |
| Polysorbate 80 | 0.30 |
| Lecithin | 4.63 |
| Citric Acid Buffer (0.025M) | 65.66 |
| Xanthan Gum | 0.43 |

TABLE 1-continued

Lecithin Based Emulsion

| Component | Wt. Percent |
|---|---|
| Sodium Benzoate | 0.05 |
| Potassium Sorbate | 0.05 |
| TOTAL | 100.00 |

*Registered trademark of Martek Biosciences Corporation

Example 3

This example illustrates the composition of a polysorbate based emulsion of the present invention in Table 2.

TABLE 2

Polysorbate Based Emulsion

| Component | Wt. Percent |
|---|---|
| DHASCO-S ®: DHA-containing oil | 27.91 |
| Polysorbate 80 | 4.92 |
| Citric Acid Buffer (0.025M) | 66.56 |
| Xanthan Gum | 0.43 |
| Sodium Benzoate | 0.05 |
| Potassium Sorbate | 0.05 |
| TOTAL | 100.00 |

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An oil-in-water emulsion, comprising:
a) an oil component from a microbial source comprising polyunsaturated fatty acids, wherein the oil component comprises a fatty acid selected from the group consisting of linolenic acid, stearidonic acid, arachidonic acid, eicosapentaenoic acid, docosapentaenoic acid, docosahexaenoic acid and mixtures thereof and wherein the microbial source is selected from the group consisting of Thraustochytriales, dinoflagellates, and fungal sources, and wherein the oil component comprises a minimum of 35% by weight docosahexaenoic acid;
b) an emulsifier;
c) an emulsion stabilizer; and
d) water,
wherein the ratio of oil component to water is between 2:1 to 1:25 and wherein the oil-in-water emulsion is physically and chemically stable for at least 30 days.

2. The oil-in-water emulsion of claim 1, wherein the oil component comprises an oil from Thraustochytriales.

3. The oil-in-water emulsion of claim 1, wherein the emulsifier is selected from the group consisting of polysorbate esters, lecithin, monoglycerides, diglycerides, organic acid esters of monoglycerides, propylene glycol esters of fatty acids, polyglycerol esters of fatty acids, propylene glycol monostearate, sorbitan monostearate, sorbitan trioleate, and sodium lauryl sulfate and mixtures thereof.

4. The oil-in-water emulsion of claim 1, wherein the stabilizer is selected from the group consisting of xanthan gum, alginate, gellan gum, carboxy methyl cellulose, chitin and mixtures thereof.

5. The oil-in-water emulsion of claim 1, wherein the weight ratio of oil component to the emulsifier is between 1:1 and 99:1.

6. The oil-in-water emulsion of claim 1, wherein the weight ratio of oil component to the emulsifier is 6:1.

7. The oil-in-water emulsion of claim 1, wherein the ratio of water to emulsion stabilizer is between 1:0.1 to 1:0.001.

8. The oil-in-water emulsion of claim 1, wherein the ratio of water to emulsion stabilizer is between 1:0.05 to 1:0.005.

9. An oil-in-water emulsion, comprising:
a) an oil component from a microbial source comprising polyunsaturated fatty acids, wherein said oil component comprises a fatty acid selected from the group consisting of linolenic acid, stearidonic acid, arachidonic acid, eicosapentaenoic acid, docosapentaenoic acid, docosahexaenoic acid and mixtures thereof and wherein said microbial source is selected from the group consisting of Thraustochytriales, dinoflagellates, and fungal sources, and wherein the oil component comprises a minimum of 35% by weight docosahexaenoic acid;
b) an emulsifier;
c) an emulsion stabilizer;
d) water; and
e) an antimicrobial component;
wherein the weight ratio of oil component to the emulsifier is between 1:1 and 99:1; wherein the ratio of water to emulsion stabilizer is between 1:0.1 to 1:0.001; wherein the ratio of oil component to water is between 2:1 to 1:25; and wherein the oil-in-water emulsion is physically and chemically stable for at least 30 days.

10. The oil-in-water emulsion of claim 9, wherein the oil component comprises an oil from Thraustochytriales.

11. A method of forming an oil-in-water emulsion, comprising combining:
a) an oil component from a microbial source comprising polyunsaturated fatty acids, wherein the oil component comprises a fatty acid selected from the group consisting of linolenic acid, stearidonic acid, arachidonic acid, eicosapentaenoic acid, docosapentaenoic acid, docosahexaenoic acid and mixtures thereof and wherein the microbial source is selected from the group consisting of Thraustochytriales, dinoflagellates, and fungal sources, and wherein the oil component comprises a minimum of 35% by weight of docosahexaenoic acid;
b) an emulsifier;
c) an emulsion stabilizer; and
d) water;
wherein the ratio of oil component to water is between 2:1 to 1:25, wherein the oil-in-water emulsion is physically and chemically stable for at least 30 days, and wherein the oil component and emulsifier are combined, the emulsion stabilizer and the water are combined; and the oil component/emulsifier combination and the emulsion stabilizer/water combination are combined.

12. The method of claim 11, wherein the oil component comprises an oil from Thraustochytriales.

13. The method of claim 11, wherein the oil component/emulsifier combination is made with high shear mixing and the combination of the oil component/emulsifier combination and the emulsion stabilizer/water combination is made with high shear mixing.

14. The method of claim 11, wherein the emulsifier is selected from the group consisting of polysorbate esters, lecithin, monoglycerides, diglycerides, organic acid esters of monoglycerides, propylene glycol esters of fatty acids, polyglycerol esters of fatty acids, propylene glycol monostearate, sorbitan monostearate, sorbitan trioleate, and sodium lauryl sulfate.

15. The method of claim 11, wherein the stabilizer is selected from the group consisting of xanthan gum, alginate, gellan gum, carboxy methyl cellulose, chitin and mixtures thereof.

16. The method of claim 11, further comprising an antimicrobial component.

17. The method of claim 11, wherein the weight ratio of oil component to the emulsifier is between 1:1 and 99:1.

18. The method of claim 11, wherein the weight ratio of oil component to the emulsifier is 6:1.

19. The method of claim 11, wherein the ratio of water to emulsion stabilizer is between 1:0.1 to 1:0.001.

20. The method of claim 11, wherein the ratio of water to emulsion stabilizer is between 1:0.05 to 1:0.005.

* * * * *